US009863874B2

(12) United States Patent
Dreyer et al.

(10) Patent No.: US 9,863,874 B2
(45) Date of Patent: Jan. 9, 2018

(54) METHOD FOR SIGNAL DETECTION IN A GAS ANALYSIS SYSTEM

(71) Applicant: Drägerwerk AG & Co. KGaA, Lübeck (DE)

(72) Inventors: Peter Dreyer, Pansdorf (DE); Livio Fornasiero, Bliestorf (DE); Arne Tröllsch, Lübeck (DE); Robert Jahns, Hernburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 15/274,305

(22) Filed: Sep. 23, 2016

(65) Prior Publication Data

US 2017/0089830 A1  Mar. 30, 2017

(30) Foreign Application Priority Data

Sep. 25, 2015 (DE) .................. 10 2015 012 429

(51) Int. Cl.
| | |
|---|---|
| *G01N 21/3504* | (2014.01) |
| *G01J 3/45* | (2006.01) |
| *G01J 3/10* | (2006.01) |
| *G01J 3/26* | (2006.01) |

(Continued)

(52) U.S. Cl.
CPC .......... *G01N 21/3504* (2013.01); *G01J 3/108* (2013.01); *G01J 3/26* (2013.01); *G01J 3/36* (2013.01); *G01J 3/42* (2013.01); *G01J 3/45* (2013.01)

(58) Field of Classification Search
CPC .......... G01N 21/3504; G01J 3/42; G01J 3/26; G01J 3/36; G01J 3/108; G01J 3/45
See application file for complete search history.

(56) References Cited

U.S. PATENT DOCUMENTS

| 7,705,991 B2 | 4/2010 | Doering et al. |
| 8,199,326 B2* | 6/2012 | Dreyer ............... G01N 21/3504 356/437 |

(Continued)

FOREIGN PATENT DOCUMENTS

| DE | 10 2006 045 253 B3 | 12/2007 |
| DE | 10 2009 011 421 B3 | 4/2010 |

*Primary Examiner* — Hwa Lee
(74) *Attorney, Agent, or Firm* — McGlew and Tuttle, P.C.

(57) ABSTRACT

A method for signal detection with a gas analysis system (1, 1') includes a radiation source (3); a gas measuring section (9) containing gas to be measured; a Fabry-Perot interferometer (13); a thermal sensor (17) configured to cause a change in voltage between electrodes with electromagnetic radiation falling thereon and arranged such that radiation released by a second interferometer mirror falls on the thermal sensor. The method includes irradiating the gas measuring section with radiation source radiation, continuously increasing or decreasing a distance of interferometer mirrors during a generating of time signal pulses at a constant period of time from one another. After a predefined number of time signal pulses, the voltage generated between the electrodes is detected and stored as a measured signal value. After a further predefined number of time signal pulses, the voltage generated between the electrodes is detected again and stored as a measured signal value.

20 Claims, 3 Drawing Sheets

(51) Int. Cl.
G01J 3/36 (2006.01)
G01J 3/42 (2006.01)

(56) References Cited

U.S. PATENT DOCUMENTS

2009/0210191 A1* 8/2009 Rogers .................... G01J 5/08
  702/134
2015/0300948 A1* 10/2015 Buchtal .............. G01N 21/3504
  356/454

* cited by examiner

METHOD FOR SIGNAL DETECTION IN A GAS ANALYSIS SYSTEM

CROSS REFERENCE TO RELATED APPLICATIONS

This application claims the benefit of priority under 35 U.S.C. §119 of German Application 10 2015 012 429.3 filed Sep. 25, 2015, the entire contents of which are incorporated herein by reference.

FIELD OF THE INVENTION

The present invention pertains to a method for signal detection in a gas analysis system for the analysis of a gas to be measured with a radiation source which emits electromagnetic radiation in a first wavelength range; with a gas measuring section, in which the gas to be measured is contained, the gas measuring section being arranged in relation to the radiation source such that the radiation emitted by the radiation source passes through the gas measuring section; with a Fabry-Perot interferometer which has a first and a second semireflecting mirror that are arranged parallel to one another, and a device for changing the distance between the mirrors, the Fabry-Perot interferometer being arranged such that radiation from the radiation source passing through the gas measuring section falls on the first mirror of the Fabry-Perot interferometer; with a thermal sensor, the thermal sensor being configured such that the electromagnetic radiation falling on it causes a change in a voltage between electrodes provided on it and being arranged such that radiation being released by the second mirror of the Fabry-Perot interferometer falls on the thermal sensor. In addition, the present invention pertains to a gas analysis system for carrying out such a method.

BACKGROUND OF THE INVENTION

A gas analysis system with a radiation source and a Fabry-Perot interferometer is known from DE 10 2006 045 253 B3, wherein the radiation from the radiation source passes through a gas measuring section in the form of a cuvette and then falls through the Fabry-Perot interferometer. The Fabry-Perot interferometer is continuously detuned with a predefined voltage, i.e., the distance of the mirrors oscillates with this voltage, and the radiation being released therefrom is detected and analyzed by a dual-band detector. In this connection, an absorption spectrum is determined by the intensity of the radiation being released from the Fabry-Perot interferometer and falling on the sensor being determined as a function of the wavelength, on which the interferometer is especially sensitive because of the distance of the mirrors.

In gas analysis systems of this type, however, the technical problem arises of achieving a reliable calibration of the sensor and of the measured values resulting from the sensor signal in relation to the wavelength and especially if thermal sensors are used which have long time constants. Such thermal sensors, such as pyroelectric detectors, must, however, frequently be used when radiation that is in the long-wave infrared range, i.e., especially in the range between 5 µm and 12 µm shall be detected. This is especially necessary if the gas analysis system shall be used for the analysis of anesthesia gas, in which the nitrous oxide and carbon dioxide contents in the breathing gas shall be determined.

Thermal sensors have, as already mentioned, a long time constant, so that they react only slowly to a change in the intensity that impinges on them. Hence, an absorption spectrum for a wavelength range with such a sensor in case of changing detuning of the Fabry-Perot interferometers and thus in case of a change in the wavelength, for which the interferometer is sensitive or which is allowed to pass through the interferometer, can only be recorded with a great expenditure of time, which would subsequently have to be analyzed in order to carry out a gas concentration determination. However, this in turn would lead to brief changes in the concentration of the gas to be analyzed being able to be detected with difficulty only.

SUMMARY OF THE INVENTION

Hence, in view of the deficiencies of the state of the art, an object of the present invention is to provide a gas analysis system and to provide a method to operate the gas analysis system with a thermal sensor such that a reliable gas concentration determination is possible in spite of the long time constant of the sensor, so that the system is consistently sensitive to the gas species that is to be analyzed with certainty.

According to the present invention, this object is accomplished by a method of signal detection including providing a gas analysis system
  with a radiation source, which emits electromagnetic radiation in a first wavelength range $\Delta\lambda 1$,
  with a gas measuring section, in which the gas to be measured is contained, the gas measuring section being arranged in relation to the radiation source such that the radiation emitted by the radiation source passes through the gas measuring section,
  with a Fabry-Perot interferometer, which has a first and a second semireflecting mirror that are arranged parallel to one another, and a device for changing the distance between the mirrors, the Fabry-Perot interferometer being arranged such that radiation from the radiation source passing through the gas measuring section falls on the first mirror of the Fabry-Perot interferometer,
  with a thermal sensor, the thermal sensor being configured such that electromagnetic radiation falling on it causes a change in a voltage between electrodes provided on it and being arranged such that radiation being released by the second mirror of the Fabry-Perot interferometer falls on the thermal sensor, wherein
  the gas measuring section is irradiated with radiation from the radiation source,
  time signal pulses are generated at a constant period of time from one another,
  the distance of the mirrors of the Fabry-Perot interferometer is continuously either increased or decreased during the generation of the time signal pulses,
  after a predefined number of time signal pulses has been generated, the voltage generated between the electrodes of the thermal sensor is detected and stored as a measured signal value, and
  after a predefined number of time signal pulses has been generated again, the voltage generated between the electrodes of the thermal sensor is detected again and stored as a measured signal value.

In the sense of the present invention, a gas measuring section is defined as only a spatial area, in which the measured gas to be analyzed is located and through which the radiation emitted by the radiation source can pass through or which this radiation can pass in order to reach the Fabry-Perot interferometer. This means that, in the present case, a gas measuring section may be a cuvette, through which the measured gas flows. However, the gas measuring section may be an open area within a production plant, in which the concentration of a gas that is relevant to safety is monitored, as this is the case in open-path systems. The present invention is, moreover, not limited to these two applications.

In the method according to the present invention, the distance between the mirrors of the Fabry-Perot interferometer is continuously increased or decreased concurrently with the generation of the time signal pulses, so that the wavelength or the wavelength interval, which is allowed to be passed through by the interferometer, is also continuously changed. The device for changing distance between mirrors of the Fabry-Perot interferometer is itself known in the art such as from U.S. Pat. No. 7,705,991 (which is incorporated herein by reference in its entirety). The radiation that has passed through the gas measuring section impinges on the Fabry-Perot interferometer, wherein a wavelength or a wavelength interval of the radiation is then allowed to pass through as a function of the distance of the mirrors and falls on the thermal sensor arranged behind (downstream with respect to the radiation path) the Fabry-Perot interferometer.

Advantage is now taken of the fact that, in the method according to the present invention, the mirror and thus the wavelength or the wavelength interval, to which the interferometer is sensitive, is a function of the time signal pulses, which are continuously generated and detected. As a result of the voltage generated at the thermal sensor being detected and stored as a measured signal value after a predefined number of pulses, an accurate wavelength interval, for which the measured signal value is an indicator of the radiation intensity detected there, can be associated with this signal. As a result of the distance of the mirrors being continuously either increased or decreased, the wavelength spectrum is also continuously passed through, the width of the wavelength sections, for each of which the intensity of the radiation impinging on the detector is detected, is determined by the selection of the time signal pulses, according to which the voltage is detected and the measured signal value is stored.

In a preferred embodiment of the method, the distance between the first and the second mirror of the Fabry-Perot interferometer depends on a voltage applied to the device for adjusting the distance, the voltage for continuously increasing or decreasing the distance being either continuously increased or continuously decreased. In such an embodiment, a control device of the gas analysis system can control the Fabry-Perot interferometer and the wavelength or the wavelength interval, in which the detector is sensitive, in a simple manner.

In another preferred embodiment, the radiation source is configured such that the intensity thereof is varied at a constant frequency, this variation being used to generate the time signal pulses. Such a configuration makes possible a detection of the time signal pulses together with the measured signal, preferably with the thermal sensor. As a result, the equipment cost is low.

Further, the thermal sensor is preferably a pyroelectric sensor, which has a crystal, on which two electrodes are mounted, wherein an electronic resetting of the signal voltage to a defined starting level can then be carried out after the detection of the voltage at the electrodes and after the storage as a measured signal value. This may, e.g., occur by the electrodes being electrically connected to one another for a period of time, the electrodes are thus short-circuited, so that the voltage between the electrodes is lowered to 0 after the period of time.

In this embodiment of the method, the pyroelectric sensor preferably used according to an embodiment of the invention is reset by the short-circuiting, so that the voltage between the electrodes is not integrated up for consecutive wavelength intervals, but for each measuring interval that corresponds to a predefined number of time signal pulses, a measured signal is stored, which is independent of the signal for the measuring interval chronologically before it.

In addition, thermal sensors and especially pyroelectric detectors have proven to be advantageous for the long-wave infrared range, i.e., for the wavelength range between 3.5 µm and 12 µm.

Further, besides a first radiation source, a second radiation source, which emits electromagnetic radiation in a second wavelength range $\Delta\lambda 2$ into the gas measuring section and which is arranged such that the radiation emitted from the second radiation source also passes through the gas measuring section and falls on the first mirror of the Fabry-Perot interferometer, may preferably also be provided. In this case, the first wavelength range $\Delta\lambda 1$, in which the first radiation source emits radiation, and the second wavelength range $\Delta\lambda 2$ differ from one another, and the intensity of the second radiation source is varied at a constant frequency in order to generate the time signal pulses.

This configuration makes it possible to use two radiation sources for the wavelength range, which is especially relevant in the case of breathing gas measurement, wherein the one radiation source can be operated with chronologically constant intensity and covers the long-wave range above 6 µm. The second radiation source, which is then preferably configured as an LED, can be used for the short-wave range between 2 µm and 6 µm. This LED can be modulated in its intensity at a constant frequency in a simple manner in order to generate the time signal pulses.

It is especially preferred to provide the LED with a collimation optics, so that a large part of the radiation generated by the diode can be focused not only in the gas measuring section, but also on the Fabry-Perot interferometer, so that the system can in turn operate efficiently.

Furthermore, in an especially preferred embodiment of the method, the Fabry-Perot interferometer may be configured as a dual-band Fabry-Perot interferometer, so that at a distance of the mirrors from one another, radiation of a first wavelength $\lambda T1$ from the first wavelength range, in a first wavelength interval, is allowed to pass through the interferometer and radiation of a second wavelength $\lambda T2$ from the second wavelength range, in a second wavelength interval, is allowed to pass through the interferometer and can then be detected by at least one sensor.

Such a configuration makes it possible to detect the intensity in two wavelength ranges in case of a predefined setting of the Fabry-Perot interferometer. In another preferred embodiment, this may occur in such a way that both intensities are detected by one and the same thermal sensor, especially a pyroelectric sensor. In addition, since the time signal pulses have been generated and at the same time a change has been made in the distance of the mirrors of the interferometer in any case, the time signal pulses can be used for calibration of the spectra in both wavelength ranges.

However, as an alternative, a second sensor may be provided, which is arranged such that radiation emitted by the second radiation source, which passes through the gas measuring section and falls on the first mirror of the Fabry-Perot interferometer, impinges on the second sensor after passing through the Fabry-Perot interferometer. This makes is possible to detect the two wavelength ranges Δλ1, Δλ2, in which the Fabry-Perot interferometer is sensitive for a wavelength interval each, separately by means of two sensors.

In this connection, it is further preferred when a beam splitter is provided, which is arranged and is configured such that a part of the radiation emitted by the radiation source or the radiation sources after passing through the gas measuring section and the Fabry-Perot interferometer falls on the first sensor and another part of this radiation falls on the second sensor. In particular, the beam splitter can be configured as a semireflecting mirror.

Further, the second sensor may especially be a semiconductor detector, which is sensitive in the infrared range and especially in the wavelength range up to 6.0 μm. A semiconductor detector has the advantage that it has a very short time constant, so that it is unproblematic to detect the time signal pulses, which are generated by modulation of the intensity of one of the radiation sources, with this detector as well.

Finally, the above object is also accomplished by a gas analysis system for analysis of a gas to be measured, and in particular comprising the system features noted with a control device controlling aspects of the method according to the present invention.

PbSe, PbS, GaAs, InAs or GaInAs may preferably be used for the active material of the semiconductor detector.

The present invention is explained below on the basis of drawings, which show the only preferred exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
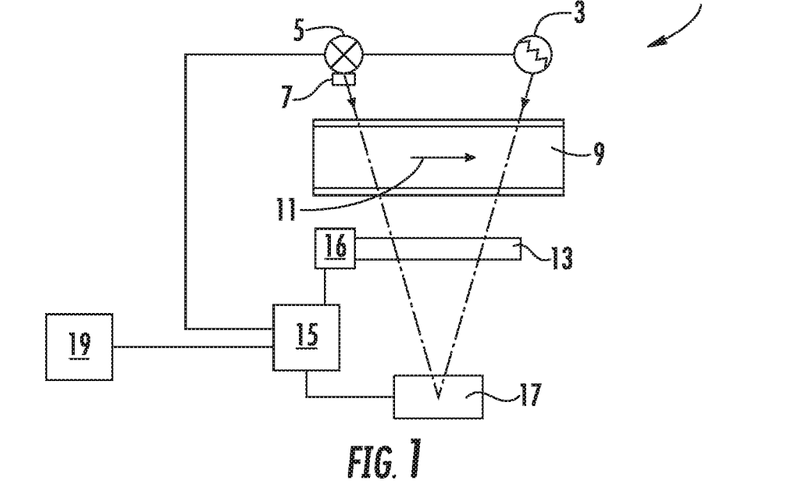
FIG. 1 is a schematic view of a first exemplary embodiment of a gas analysis system for carrying out the method according to the present invention.

Referring to the drawings, a first preferred exemplary embodiment of a gas analysis system for carrying out the method according to the present invention shown in FIG. 1 has a first thermal radiation source 3 as well as a second radiation source 5, configured as an LED. In this exemplary embodiment the first radiation source 3 emits radiation in a first wavelength range Δλ1 between 3.5 μm and 12 μm. The second radiation source 5, which has its characteristic emission spectrum in a second wavelength range Δλ2 of 2 μm to 6 μm, is, in addition, equipped with a collimation optics 7 in this preferred exemplary embodiment, so that the radiation emitted by the second radiation source 5 is radiated out in only one direction. It is, however, radiation sources with other emission wavelengths may also be used.

The gas analysis system 1 has a gas measuring section in the form of a measuring cuvette 9, through which the gas to be measured and to be analyzed can flow along a flow direction 11. In this case, the cuvette 9 and thus the gas measuring section is arranged such that radiation emitted by the radiation sources 3, 5 passes through the cuvette 9. In particular, the direction, in which the radiation of the second radiation source 5 is emitted by the collimation optics 7, is directed toward the cuvette 9. On the side of the cuvette 9 located opposite the radiation sources 3, 5, a dual-band Fabry-Perot interferometer 13 is arranged, which has two semireflecting mirrors running parallel to one another, wherein the distance between the mirrors can be changed with a distance adjustment device 16 configured to change a distance between the mirrors and controlled by means of a control device 15 configured as discussed below and which, in addition, is connected to the first and to the second radiation source 3, 5. For this, a voltage signal is transmitted by the control device 15 to a device for changing the distance adjustment device 16 at the interferometer 13.

In addition, the gas analysis system 1 has a thermal sensor in the form of a pyroelectric detector 17, which is arranged such that radiation both of the first and of the second radiation source 3, 5 being released by the second mirror of the Fabry-Perot interferometer 13 falls on the thermal sensor or the pyroelectric detector 17.

The thermal sensor or pyroelectric detector 17 has a crystal, on which two electrodes are mounted, wherein a change in voltage between the electrodes is set based on the heat energy introduced by impinging electromagnetic radiation. This voltage signal can be detected by the control device 15 and be forwarded to an analysis device 19, to which the control device 15 is connected. In this case, the pyroelectric detector 17 is sensitive both in the first wavelength range Δλ1, in which the first radiation source 3 emits, and in the second wavelength range Δλ2, in which the second radiation source 5 emits.

FIGS. 3a-3d shows a preferred embodiment of the method and the configured control device 15 according to the present invention, according to which the first exemplary embodiment of the gas analysis system 1 from FIG. 1 is operated.

Figure 3A:
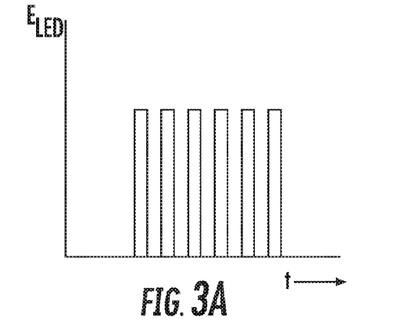
FIG. 3a is a diagram showing a course over time of the radiation intensity of a second radiation source during the operation of the exemplary embodiment from FIG. 1.
Figure 3B:
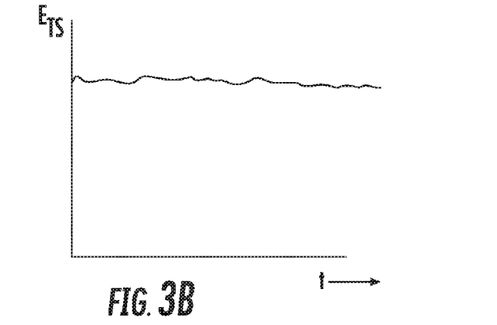
FIG. 3b is a diagram showing a course over time of the radiation intensity of a first thermal radiation source during the operation of the exemplary embodiment from FIG. 1.

It is shown in FIG. 3a what course over time the intensity of the second radiation source 5, which is configured as an LED, has, while FIG. 3b shows the course over time of the first thermal radiation source 3. It can be seen from this that the intensity of the second radiation source 5, which emits radiation in the second wavelength range $\Delta\lambda 2$, is varied at a constant frequency, so that individual pulses are emitted at this frequency. As a result, time signal pulses are generated at a constant time interval from one another. By contrast, the first radiation source 3 emits infrared radiation with an almost constant intensity over time in the first wavelength range $\Delta\lambda 1$.

Figure 3C:
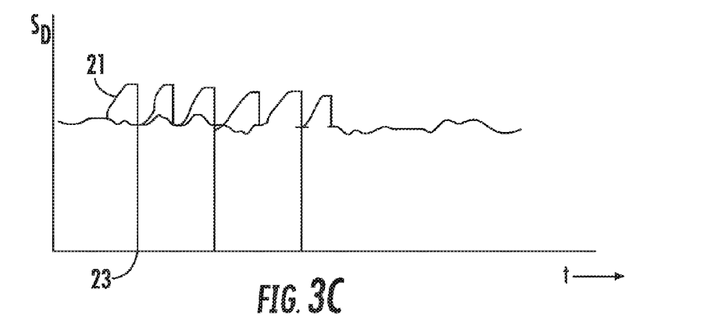
FIG. 3c is a diagram showing a signal sent by the pyroelectric detector as a function of time.

FIG. 3c shows the signal sent by the pyroelectric detector 17 as a function of time in the embodiment of the method according to the present invention. Time signal pulses are generated at a constant time interval by the modulation of the second radiation source 5 and, in addition, the distance of the mirrors of the dual-band Fabry-Perot interferometer 13 are continuously increased in this embodiment. However, the distance may instead be continuously decreased.

Due to the change in the distance of the mirrors of the dual-band Fabry-Perot interferometer 13, the wavelength intervals, which are allowed to be passed through by the interferometer and strike the pyroelectric detector 17, change by a first and a second wavelength $\lambda T1$, $\lambda T2$ from the first wavelength range $\Delta\lambda 1$ and from the second wavelength range $\Delta\lambda 2$. The intensity as a function of time is thus also an intensity as a function of the wavelength and thus a transmission spectrum for both wavelength ranges $\Delta\lambda 1$, $\Delta\lambda 2$.

Because of a long time constant compared to the actual course of the intensity of the radiation from the first and second radiation source 3, 5, which impinges on the pyroelectric detector 17, the signal of the pyroelectric detector 17 is markedly changed. However, because of the intensity of the second radiation source 5, which is varied at a constant frequency, this signal also has a modulation with precisely this frequency. While the time signal pulses are generated and are also detected by the detector 17 and the control device 15 by means of the modulation of the second radiation source 5, the signal at first increases in a first section 21 until the two electrodes of the pyroelectric detector 17 are short-circuited for a predefined period of time after a predefined number of time signal pulses, i.e., radiation pulses of the second radiation source 5, so that the voltage at time 23 at first drops to zero as a defined starting level. The voltage value present before the short-circuiting is forwarded as a measured signal value by the control device 15 to the analysis device 19 and stored.

In this way, the method is carried out again after another predefined number of time signal pulses, so that the pattern shown in FIG. 3c is obtained.

Due to the use of the modulated and pulsed radiation of the second radiation source 5, time signal pulses are provided, the number of time signal pulses being an indicator of the wavelength interval, for which the dual-band Fabry-Perot interferometer 13 is reflective or to which it is tuned, so that a reliable calibration, which applies both to the first and to the second wavelength range $\Delta\lambda 1$, $\Delta\lambda 2$, is provided as a result. By a number of time signal pulses also being associated with each measured signal value, it can be determined for which two intervals in the first and second wavelength range $\Delta\lambda 1$, $\Delta\lambda 2$ the respective measured signal value represents a mean value.

In order to resolve the time signal pulses from the signal of the pyroelectric detector 17, in the first exemplary embodiment described according to the invention, the signal of the detector 17 detected by the control device 15 is filtered by means of a bandpass filter, which varies at the frequency, with which the second radiation source 5 emits radiation in the second wavelength range $\Delta\lambda 2$ and from which the time signal pulses can be extracted.

Figure 3D:
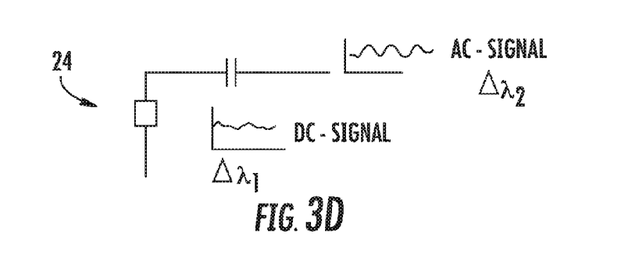
FIG. 3d is a schematic view showing features for separating an intensity detected by the pyroelectric detector with respect to the first and second wavelength range.

FIG. 3d schematically shows a possibility for separating the intensity detected by the pyroelectric detector 17 to the first and second wavelength range $\Delta\lambda 1$, $\Delta\lambda 2$. The signal component (DC signal), which is relevant for the first wavelength range $\Delta\lambda 1$, is a direct current signal, since this traces back to radiation from the first radiation source 3. By contrast, the signal component, which is relevant for the second wavelength range $\Delta\lambda 2$, is an alternating current signal (AC signal) at the frequency, at which the second radiation source 5 is modulated. A separation of the DC signal from the AC signal is carried out by, e.g., an RC combination 24, which forms an electronic bandpass. The AC signal relevant for the second wavelength range $\Delta\lambda 2$ is analyzed by means of the lock-in method, i.e., in-phase rectification of the AC signal is carried out by means of the actuating frequency of the second radiation source 5, which serves as a reference frequency. The change in the amplitude of the measured AC signal and thus its in-phase-rectified value is an indicator of the received intensity of the radiation on the second wavelength range $\Delta\lambda 2$ and thus an indicator of the gas concentration. The DC signal is, on the other hand, an indicator of the received intensity of the radiation in the first wavelength range.

Figure 2:
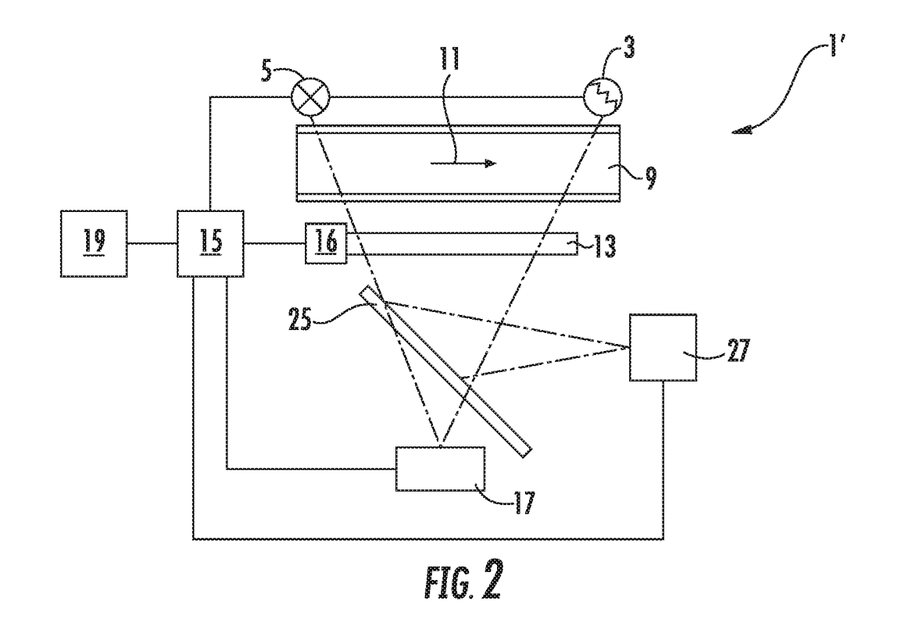
FIG. 2 is a schematic view of a second exemplary embodiment of a gas analysis system.

FIG. 2 shows a second exemplary embodiment of a gas analysis system 1', which likewise has a first and a second radiation source 3, 5, the first radiation source 3 being configured as a thermal radiation source, which emits infrared light in a first wavelength range $\Delta\lambda 1$ of 3.5 µm to 12 µm. The second radiation source 15 is in turn configured as an LED and emits radiation in a second wavelength range $\Delta\lambda 2$ between 2 µm and 6 µm. The radiation of the two radiation sources 3, 5 passes through a cuvette 9 forming a gas measuring section and falls on a dual-band Fabry-Perot interferometer 13, which is arranged on the side of the cuvette 9 located opposite the radiation sources 3, 5.

The dual-band Fabry-Perot interferometer 13 has in turn a first and a second semireflecting mirror with a distance adjustment device 16 configured to change a distance between the mirrors, shown schematically. The distance between the first and the second semireflecting mirrors can be varied by means of a control device 15 and the distance adjustment device 16 for changing distance provided at the interferometer 13, wherein a voltage is applied by the control device 15 to the distance adjustment device 16 at the dual-band Fabry-Perot interferometer 13. In particular, the distance changes with the voltage. By the distance of the mirrors of the dual-band Fabry-Perot interferometer 13 being changed, the wavelength intervals are also changed by the wavelengths $\lambda T1$, $\lambda T2$ from the first and second wavelength range $\Delta\lambda 1$, $\Delta\lambda 2$, which are allowed to be passed through by the dual-band Fabry-Perot interferometer 13 and are released from the second semireflecting mirror of the interferometer 13.

Radiation being released from the second, semireflecting mirror of the Fabry-Perot interferometer 13 falls on a beam splitter 25, which is configured as a semireflecting mirror. Radiation passing through the beam splitter 24 unreflected falls in turn on a thermal sensor configured as a pyroelectric detector 17 which has a crystal with two electrodes, between which an electric voltage, which arises due to the absorption of the radiation energy in the material of the crystal of the thermal sensor, is generated in case of radiation falling on the pyroelectric detector 17.

The radiation reflected by the beam splitter 25 falls on a second sensor, which is configured as a semiconductor detector 27, which has a very short time constant and is sensitive for radiation in the second wavelength range $\Delta\lambda 2$, i.e., in the range of up to 6 μm, in which the second radiation source 5 also emits. PbSe, PbS, GaAs, InAs or GaInAs may preferably be used as active material in the semiconductor detector 27. In addition, the semiconductor detector 27 is connected to the control device 15, as are the first and the second radiation sources 3, 5 as well.

It can be seen from FIGS. 4a-4g how in a second preferred embodiment of the method according to the present invention, the second exemplary embodiment of a gas analysis system 1' can be operated and a preferred second embodiment of the method and the configured control device 15 according to the present invention.

Figure 4A:
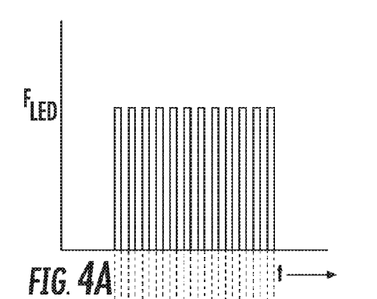
FIG. 4a is a diagram showing a course over time of the radiation intensity of the second radiation source during the operation of the exemplary embodiment from FIG. 2.

FIG. 4a shows the course over time of the intensity of the radiation of the second radiation source 5, which is configured as an LED and emits radiation in the second wavelength range $\Delta\lambda 2$ up to 4.5 μm, wherein it can be seen that this emitted radiation occurs pulsed at a fixed frequency, so that time signal pulses with at a fixed time interval are continuously generated by the second radiation source 5 as a result.

Figure 4B:
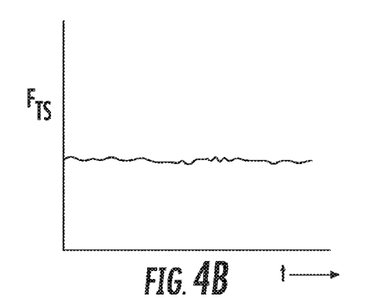
FIG. 4b is a diagram showing a course over time of the radiation intensity of a first radiation source during the operation of the exemplary embodiment from FIG. 2.

By contrast, the course over time of the intensity of the first radiation source 3 is constant, as is shown in FIG. 4b of FIG. 4.

Figure 4C:
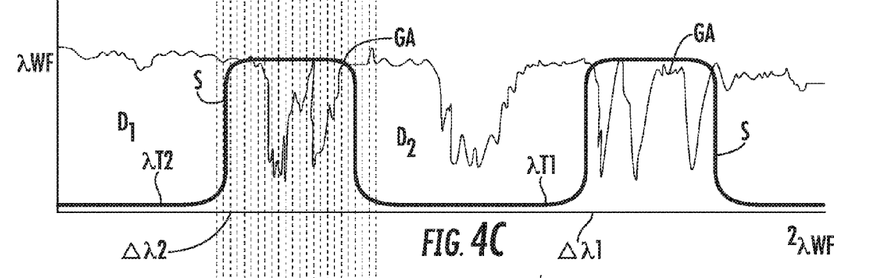
FIG. 4c is a diagram showing, with a line designated by GA, the absorption curve of the gas to be measured as a function of the wavelength.

FIG. 4c shows, by means of the line designated by GA, the absorption curve of the gas to be measured as a function of the wavelength, absorption lines of the gas to be measured lying both in the first wavelength range $\Delta\lambda 1$ and in the second wavelength range $\Delta\lambda 2$. Hence, the dual-band Fabry-Perot interferometer 13 is set by selecting the value range which the distance of the mirrors can be from one another such that the interferometer 13 is operated in a way that it has a sensitivity, which is shown by the line designated by "S." The areas, in which the absorption lines of relevant components of the gas to be measured lie, are thus especially detected in the first and the second wavelength range $\Delta\lambda 1$, $\Delta\lambda 2$, so that the concentration of these components in the gas to be measured can be derived therefrom.

In the operation of the gas analysis system 1' from FIG. 2, the LED forming the second radiation source 5 is modulated, as described, at the fixed frequency, the time signal pulses being generated as a result. In addition, the distance of the mirrors of the dual-band Fabry-Perot interferometer 13 are set concurrently with the generation of the time signal pulses such that radiation in a first wavelength interval is allowed to be passed through by a first wavelength $\lambda T1$ in the first wavelength range $\Delta\lambda 1$ and in a second wavelength interval by a second wavelength $\lambda T2$ in the second wavelength range $\Delta\lambda 2$ and falls on the beam splitter 25, from which the radiation strikes the two detectors 17, 27. The pyroelectric detector 17 then detects the intensity in the first wavelength interval by the first wavelength $\lambda T1$, while the semiconductor detector 27 detects the intensity in the second wavelength interval by the second wavelength $\lambda T2$, the second sensor configured as a semiconductor detector 27 having a sufficiently short time constant in order to be able to resolve the pulses of the second radiation source 5 over time. Thus, the time signal pulses can readily also be detected by the control device 15.

Concurrently with the pulsed or intensity-modulated operation of the second radiation source 5 and the generation of the time signal pulses connected thereto, the distance of the mirrors of the dual-band Fabry-Perot interferometer 13 is also continuously increased in this exemplary embodiment, so that the wavelengths of the radiation from the first and the second wavelength range $\Delta\lambda 1$, $\Delta\lambda 2$, which falls from the interferometer 13 on the beam splitter 25, is shifted toward longer wavelengths. The increase in the distance of the mirrors is achieved by changing a control voltage, which is sent by the control device 15 to distance adjustment device 16 at the dual-band Fabry-Perot interferometer 13.

By increasing the distance of the mirrors concurrently with generating the time signal pulses, the number of detected time signal pulses represents an indicator of the change in the wavelengths, at which the detectors 17, 27 are sensitive because of the setting of the interferometer 13, and thus makes possible a simple calibration of the measured signal values. This occurs as follows:

After a predefined number of time signal pulses, which may be different for the pyroelectric detector 17 and the semiconductor detector 27 but are detected by the "fast" semiconductor detector 27 in any case, the measured signals of the detectors 17, 27 are stored by the analysis device 19 as measured signal values together with the number of time signal pulses since the start of the measurement. In this case, the also stored number of time signal pulses is the indicator of the wavelength, for which the measured signal value is an indicator of the intensity detected at the respective detector 17, 27.

Figure 4D:
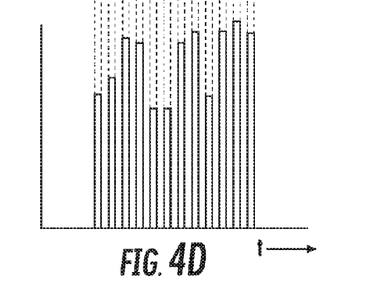
FIG. 4d is a diagram showing measured signal values detected and stored at the semiconductor detector.

The measured signal values detected and stored at the semiconductor detector 27 are shown in FIG. 4d. The measured signal values detected and stored at the pyroelectric detector 17 are shown in FIG. 4e, wherein it can be seen at first that the number of time signal pulses, after which a measured signal value is stored at the pyroelectric detector 17, is greater than in case of the semiconductor detector 27, since the pyroelectric detector 17 with its 20-dB characteristic acts as an integrator.

Figure 4E:
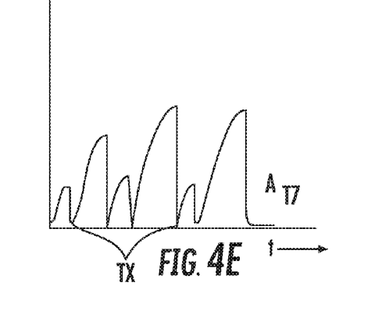
FIG. 4e is a diagram showing measured signal values detected and stored at the pyroelectric detector.

Furthermore, it can be seen from FIG. 4e that the signal of the thermal sensor configured as a pyroelectric detector 17 at times TX, each after the predefined number of time signal pulses has been detected for the pyroelectric detector 17, drops to zero. This is attributable to the fact that after the predefined number of time signal pulses, the electrodes of the pyroelectric detector 17 are always short-circuited for a period of time, so that the voltage, which has formed between the electrodes, has dropped to zero. It is thus achieved that the pyroelectric detector 17 is reset and the voltage building up during the predefined number of time signal pulses can always be detected as a measured signal value.

Figure 4F:
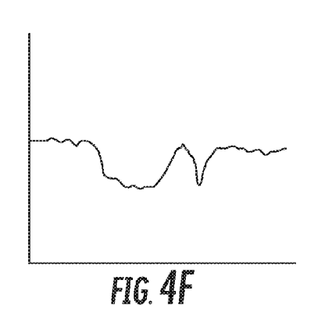
FIG. 4f is a diagram showing measured signal values stored by analysis device for the semiconductor detector.
Figure 4G:
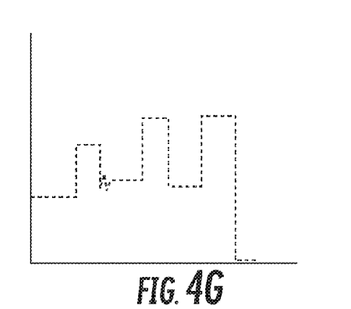
FIG. 4g is a diagram showing measured signal values stored by analysis device for the pyroelectric detector.

FIG. 4f and FIG. 4g each show the measured signal values stored by analysis device 19 for the pyroelectric detector 17 (FIG. 4g) and for the semiconductor detector 27 (FIG. 40.

Because of the detected number of time signal pulses generated, which pulses lie between the detected measured signal values, a wavelength calibration is obtained, wherein the number of time signal pulses detected with the semiconductor detector 27 at the same time makes possible a calibration of the measured signal values, which are detected at the detectors 17, 27.

While specific embodiments of the invention have been shown and described in detail to illustrate the application of the principles of the invention, it will be understood that the invention may be embodied otherwise without departing from such principles.

What is claimed is:

1. A method for signal detection in the analysis of a gas to be measured, the method comprising the steps of:
   providing a gas analysis system comprising:
   a radiation source, which emits electromagnetic radiation in a first wavelength range;
   a gas measuring section, in which the gas to be measured is contained, the gas measuring section being arranged in relation to the radiation source such that the radiation emitted by the radiation source passes through the gas measuring section;
   a Fabry-Perot interferometer comprising a first semireflecting mirror, a second semireflecting mirror arranged parallel to the first semireflecting mirror and a distance adjustment device configured to change a distance between the mirrors, the Fabry-Perot interferometer being arranged such that radiation from the radiation source passing through the gas measuring section falls on the first mirror of the Fabry-Perot interferometer; and
   a thermal sensor configured such that the electromagnetic radiation falling on the thermal sensor causes a change in a voltage between electrodes provided on the thermal sensor and being arranged such that radiation being released by the second mirror of the Fabry-Perot interferometer falls on the thermal sensor;
   irradiating the gas measuring section with radiation from the radiation source;
   generating time signal pulses at a constant period of time from one another;
   continuously either increasing or decreasing the distance between the minors of the Fabry-Perot interferometer during the generation of the time signal pulses;
   detecting and storing the voltage generated between the electrodes of the thermal sensor as a measured signal value after a predefined number of time signal pulses has been generated; and
   again detecting and storing the voltage generated between the electrodes of the thermal sensor as a measured signal value after another predefined number of time signal pulses has been generated.

2. A method in accordance with claim 1, wherein:
   the distance between the first mirror of the Fabry-Perot interferometer and the second mirror of the Fabry-Perot interferometer is dependent upon an applied voltage, which applied voltage is applied to the distance adjustment device; and
   the applied voltage for the continuous increasing or decreasing of the distance is either continuously increased or continuously decreased.

3. A method in accordance with claim 1, wherein the time signal pulses are generated by varying an intensity of the radiation source at a constant frequency.

4. A method in accordance with claim 1, wherein:
   the thermal sensor is a pyroelectric sensor comprising a crystal on which the two electrodes are mounted; and
   after detecting and storing the voltage as a measured signal value, a signal voltage of the thermal sensor is reset to a defined starting level, whereby the voltage between the electrodes is lowered to defined starting level after a period of time.

5. A method in accordance with claim 1, wherein the radiation source is an infrared radiation source, which emits electromagnetic radiation in the wavelength range of 3.5 µm to 12 µm.

6. A method in accordance with claim 1, wherein:
   the gas analysis system further comprises a second radiation source, which emits electromagnetic radiation in a second wavelength range into the gas measuring section and which is arranged such that radiation emitted from the second radiation source passes through the gas measuring section and falls on the first mirror of the Fabry-Perot interferometer;
   the second wavelength range and the first wavelength range differ from one another; and
   an intensity of the second radiation source is varied at a constant frequency in order to generate the time signal pulses of radiation in a second wavelength range.

7. A method in accordance with claim 6, wherein the second radiation source is an LED, which has its characteristic emission spectrum in the wavelength range of 2 µm to 6 µm.

8. A method in accordance with claim 7, wherein the LED has a collimation optics.

9. A method in accordance with claim 6, wherein the Fabry-Perot interferometer is configured as a dual-band Fabry-Perot interferometer, whereby at a predefined distance of the mirrors from one another, radiation in a first wavelength interval is allowed to pass through the interferometer by a first wavelength from the first wavelength range and radiation in a second wavelength interval is allowed to pass through the interferometer by a second wavelength from the second wavelength range.

10. A method in accordance with claim 6, wherein the radiation emitted by the second radiation source impinges on the thermal sensor after passing through the Fabry-Perot interferometer.

11. A method in accordance with claim 6, wherein the gas analysis system comprises a second sensor arranged such that radiation emitted by the second radiation source, which passes through the gas measuring section and falls on the first mirror of the Fabry-Perot interferometer, impinges on the second sensor after passing through the Fabry-Perot interferometer.

12. A method in accordance with claim 11, wherein a beam splitter is provided, which is arranged and configured such that a part of the radiation falls on the first sensor after passing through the Fabry-Perot interferometer and a part of the radiation falls on the second sensor after passing through the Fabry-Perot interferometer.

13. A method in accordance with claim 11, wherein the second sensor is a semiconductor detector, which semiconductor detector is sensitive in the infrared range, in a wavelength range up to 6.0 µm.

14. A method in accordance with claim 13, wherein the semiconductor detector has PbSe, PbS, GaAs, InAs or GaInAs as active material.

15. A gas analysis system for an analysis of a gas to be measured, the system comprising:
   a radiation source, which radiation source emits electromagnetic radiation in a first wavelength range;
   a gas measuring section, in which the gas to be measured is contained, the gas measuring section being arranged in relation to the radiation source such that the radiation emitted by the radiation source passes through the gas measuring section;
   a Fabry-Perot interferometer comprising a first semireflecting mirror and a second semireflecting mirror arranged parallel to the first semireflecting mirror, and a distance adjustment device configured to change a distance between the first semireflecting mirror and the second semireflecting mirror, the Fabry-Perot interferometer being arranged such that radiation from the radiation source passing through the gas measuring section falls on the first mirror of the Fabry-Perot interferometer;

a thermal sensor configured such that the electromagnetic radiation falling on the thermal sensor causes a change in a voltage between electrodes provided on thermal sensor and being arranged such that radiation being released by the second mirror of the Fabry-Perot interferometer falls on the thermal sensor; and a control device connected to the radiation source, connected to the Fabry-Perot interferometer and connected to the thermal sensor, the control device being configured to:

control an irradiating of the gas measuring section with radiation from the radiation source;

control a generating of time signal pulses at a constant period of time from one another;

control the distance of the mirrors of the Fabry-Perot interferometer to either continuously increase or continuously decrease the distance during the generation of the time signal pulses;

detect and store the voltage generated between the electrodes of the thermal sensor as a measured signal value after a predefined number of time signal pulses has been generated; and again detect and store the voltage generated between the electrodes of the thermal sensor as a measured signal value after another predefined number of time signal pulses has been generated.

16. A gas analysis system in accordance with claim 15, wherein:

the control device controls the distance between the first mirror of the Fabry-Perot interferometer and the second mirror of the Fabry-Perot interferometer dependent upon an applied voltage, which applied voltage is applied to the distance adjustment device; and control device continuously increases or continuously decreases the applied voltage.

17. A gas analysis system in accordance with claim 15, wherein the time signal pulses are generated by varying an intensity of the radiation source at a constant frequency.

18. A gas analysis system in accordance with claim 15, wherein:

the thermal sensor is a pyroelectric sensor comprising a crystal on which the two electrodes are mounted; and the control device, after detecting and storing the voltage as a measured signal value, resets a signal voltage of the thermal sensor to a defined starting level, whereby the voltage between the electrodes is lowered to defined starting level after a period of time.

19. A gas analysis system in accordance with claim 15, further comprising a second radiation source, which emits electromagnetic radiation in a second wavelength range into the gas measuring section and which is arranged such that radiation emitted from the second radiation source passes through the gas measuring section and falls on the first mirror of the Fabry-Perot interferometer, wherein:

the second wavelength range and the first wavelength range differ from one another; and an intensity of the second radiation source is varied at a constant frequency in order to generate time signal pulses of radiation in a second wavelength range.

20. A gas analysis system in accordance with claim 19, wherein the Fabry-Perot interferometer is configured as a dual-band Fabry-Perot interferometer, whereby at a predefined distance of the mirrors from one another, radiation in a first wavelength interval is allowed to pass through the interferometer by a first wavelength from the first wavelength range and radiation in a second wavelength interval is allowed to pass through the interferometer by a second wavelength from the second wavelength range and the gas analysis system further comprises:

a second sensor arranged such that radiation emitted by the second radiation source, which passes through the gas measuring section and falls on the first mirror of the Fabry-Perot interferometer, impinges on the second sensor after passing through the Fabry-Perot interferometer; and a beam splitter arranged and configured such that a part of the radiation falls on the first sensor after passing through the Fabry-Perot interferometer and a part of the radiation falls on the second sensor after passing through the Fabry-Perot interferometer.

* * * * *